(12) United States Patent
Vaishnav et al.

(10) Patent No.: US 7,566,792 B2
(45) Date of Patent: Jul. 28, 2009

(54) METHOD FOR THE MANUFACTURE OF LOVASTATIN

(75) Inventors: Sanjay Kumar Vaishnav, Maharashtra (IN); Bhupendra Harishchandra Thakur, Maharashtra (IN); Subhash Rajaram Kadam, Maharashtra (IN)

(73) Assignee: Lupin Limited, Mumbai, Maharashtra (IN)

( * ) Notice: Subject to any disclaimer, the term of this patent is extended or adjusted under 35 U.S.C. 154(b) by 52 days.

(21) Appl. No.: 10/571,192

(22) PCT Filed: Oct. 14, 2003

(86) PCT No.: PCT/IN03/00333

§ 371 (c)(1),
(2), (4) Date: Dec. 20, 2006

(87) PCT Pub. No.: WO2005/035515

PCT Pub. Date: Apr. 21, 2005

(65) Prior Publication Data

US 2007/0238885 A1    Oct. 11, 2007

(51) Int. Cl.
*C07D 309/30* (2006.01)
(52) U.S. Cl. ...................................................... 549/292
(58) Field of Classification Search ................. 549/292
See application file for complete search history.

(56) References Cited

U.S. PATENT DOCUMENTS 7,052,886 B2 * 5/2006 Kumar et al. ................ 435/125
2002/0156298 A1 10/2002 McManus et al.

FOREIGN PATENT DOCUMENTS

EP       1 110 959    6/2001
WO      97/20834     6/1997

* cited by examiner

*Primary Examiner*—D. Margaret Seaman
*Assistant Examiner*—Nizal S Chandrakumar
(74) *Attorney, Agent, or Firm*—Ladas & Parry LLP

(57) ABSTRACT

A method for the manufacture of Lovastatin of formula (I) is disclosed. The method comprises of: A. lactonisation of Mevinolinic acid (II) and isolation of impure Lovastatin (I), B. purification of impure Lovastatin (I), C. optionally, repurification of pure Lovastatin (I) from a mixture of alumina and a water miscible solvent.

14 Claims, 3 Drawing Sheets ii) Recrystallisation of Lovastatin (I) from isopropanol [obtained in step B (i)]
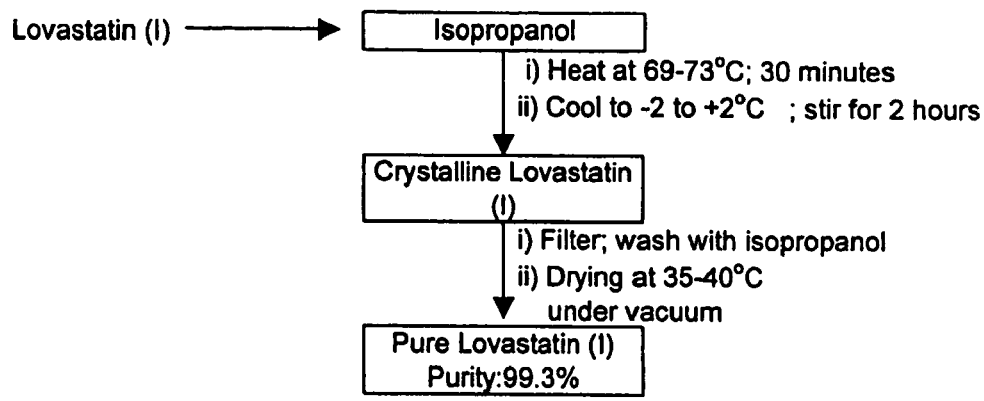
C). PURIFICATION OF LOVASTATIN(I) [as obtained in step B(ii)] (Optional)
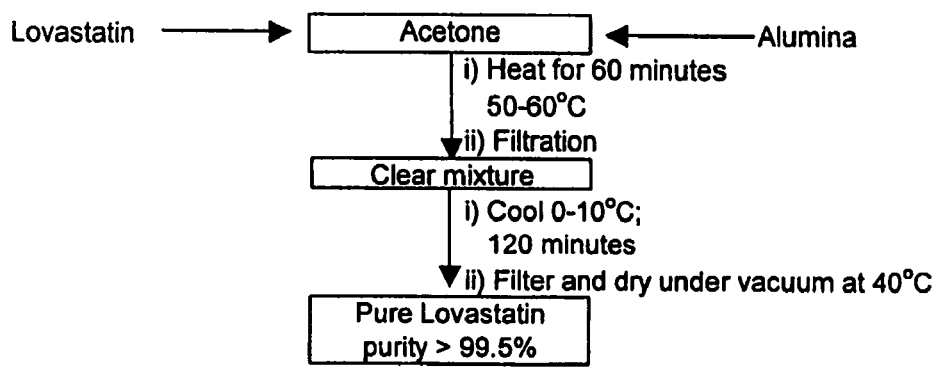
FIG. 1 ...contd

METHOD FOR THE MANUFACTURE OF LOVASTATIN

FIELD OF INVENTION

The present invention relates to an improved method for manufacture of Lovastatin (I) and its isolation in high purity, substantially free of impurities.

BACKGROUND OF THE INVENTION

Lovastatin or Mevinolin represented by formula (I) is a valuable hypocholesteremic drug, which inhibits biosynthesis of cholesterol by competitively inhibiting 3-hydroxy-3-methylglutaryl-coenzyme A reductase (HMG-CoA reductase). Its inhibition leads to reduction in the rate of formation of cholesterol in the human body.

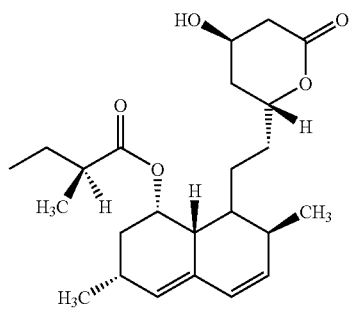

(I)

Lovastatin of formula (I) known chemically as (1S, 3R, 7S, 8S, 8a R)1,2,3,7,8,8a-hexahydro-3,7-dimethyl-8-[2-[(2R, 4R)tetrahydro-4-hydroxy-6-oxo-2H-pyran-2-yl]ethyl]-1-napthalenyl-(S) -2-methylbutyrate is disclosed in U.S. Pat. No. 4,231,938.

Generally, Lovastatin of formula (I) is obtained through fermentation, comprising cultivating a microorganism belonging to the genus Aspergillus in an aqueous medium containing carbohydrates, yeast, inorganic salts like sodium chloride, ammonium phosphate etc assimilable by the microorganism.

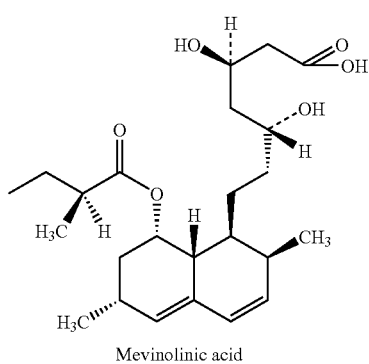

Mevinolinic acid (II)

The fermentation is generally carried out at ambient temperature, preferably, between 20-37° C. and pH range of 6.0 to 8.0, to give mevinolinic acid of formula (II). Lovastatin (I) is obtained and isolated from the fermentation broth after lactonisation of the acid (II) in the presence of an acid.

Several methods are known for isolation of Lovastatin (I) through lactonisation of Mevinolinic acid (II), which are summarized herein below:

1. U.S. Pat. No. 4,231,938 (Monaghan R. L et al) describes a method for isolation of Lovastatin (I) from a fermentation broth which comprises obtaining Mevinolinic acid (II) by fermentation from an aqueous medium containing a microorganism known as *Aspergillus terreus* and sources of carbon, nitrogen and inorganic salts assimilable by the microorganism. The fermentation is carried out between pH 6.0 to 8.0 and temperature range of 20-37° C. The broth containing Mevinolinic acid (II) is filtered and acidified to pH 4.0 with concentrated hydrochloric acid and extracted with ethyl acetate. Evaporation of the organic layer gives impure Lovastatin (I) as syrupy oil, which is then purified by column chromatography on silica gel.

However, this method has little industrial application since it involves purification by chromatography.

2. BG60460A (T. G. Dimitar et al) teaches a method for isolation of Lovastatin (I), which comprises alkaline treatment of the cultured broth at pH 8.5-9.0 followed by filtration, acidification and extraction with an organic solvent. The organic extract after concentration is purified by ultrafiltration/reverse osmosis and finally recrystallised from ethyl acetate, butyl acetate or ethanol.

The purification method involving reverse filtration or reverse osmosis, is however not attractive for industrial manufacture.

3. PCT Application No WO 97/20834 A1. (Dimov I et al) describes a method for isolation of Lovastatin (I) from the culture broth which comprises treatment of the broth with an alkaline base in the presence of an anti-oxidant and inert filler, between pH 9.5-13.0 after which the fermentation broth is filtered and the mycelia cake is washed with a dilute solution of an alkaline base. The mixture thus obtained is acidified with a mineral acid between pH 2.5-4.0 to give Mevinolinic acid (II), which is filtered and dissolved in a chlorinated hydrocarbon. The acid (II) is lactonised by heating the mixture to give Lovastatin (I), which is then concentrated. The impure product (I) is recrystallized several times from a mixture of acetonitrile, tert-butylmethyl ether, and butyl chloride.

The method, however, suffers from the following shortcomings in that, it is lengthy involving additional unit operations of alkaline pretreatment of the culture broth with a base followed by acidification and filtration to give Mevinolinic acid (II). Moreover, it utilizes acetonitrile, which has a low flash point i.e. 2° C., which renders its use on a commercial scale a hazardous proposition.

4. U.S. Pat. No. 5,202,029 (Haytko P. N et al) claims a method for purification of Lovastatin (I) using high performance liquid chromatography (HPLC). This method of purification is not suited for industrial use due to its high cost.

5. U.S. Pat. No. 5,712,130 (Hajko P et al) discloses a method for isolation of Lovastatin (I) by extracting the acidified fermentation broth containing Mevinolinic acid (II) with butyl acetate. The organic layer is concentrated under reduced pressure above 40° C., during which lactone formation takes place with simultaneous removal of water giving Lovastatin (I) with purity of 90%.

6. U.S. Pat. No. 6,387,258 B1 (K. Vilmos et al) describes a method of isolation and purification of statin compounds which comprises alkaline pretreatment of the fermentation broth in the presence of a hydrophobic solvent like isobutyl acetate and a de-emulsifier like dodecyl trimethyl ammonium chloride. The purified fermentation broth after acidification to pH between 2.0-4.5 with sulfuric acid is extracted with isobutyl acetate and the organic extract concentrated to give impure Lovastatin (I) which is purified by recrystallisation from ethanol/water mixture. The procedure is, however, lengthy involving multiple steps of initial alkaline pretreatment, acidification, lactonisation and isolation of impure Lovastatin (I), and therefore, less attractive for industrial manufacture. It is pertinent to mention that the isolated yield of Lovastatin (I) is quite low, without alkaline pretreatment of the fermentation broth.

7. U.S. Patent Application 2002/0156298 A1 (McManus, J et al) teaches a method for lactonisation of Mevinolinic acid (II) wherein the lactonisation is carried out with a strong mineral acid at a temperature lower than 10° C. in presence of solvents like acetonitirile, dimethyl sulfoxide, tetrahydrofuran and dioxane.

8. U.S. patent application Ser. No. 5,917,058 (Y. Kumar, et al) describes a method for isolation of Lovastatin (I) using acetic acid as solvent in absence of strong acid with mild heating till 55° C.

However, isolation of Lovastatin (I) by this method is tedious since it involves removal of excess acetic acid by neutralization with a base, which results in salts of acetic acid, which have to be removed thoroughly prior to crystallisation of Lovastatin (I). Another drawback is the impurity formation resulting from the esterification reaction between 3-hydroxy group of the 3-hydroxy lactone and acetic acid.

9. U.S. patent application Ser. No. 5,939,564 (Y. Kumar, et al) teaches a method for lactonisation of Mevinolinic acid (II) to give Lovastatin (I) using a mild catalyst such as a pyridine salt of a mineral or organic acid for carrying out the transformation. The lactonisation is carried out in a polar alcoholic or non-alcoholic solvent at 42-45° C. and the resulting Lovastatin (I) is isolated by addition of water.

10. US Patent Application 2002/0147351 A1 (T. H. A Peters, et al) teaches a method for isolation of Lovastatin (I) by lactonisation of Mevinolinic acid (II) or its ammonium salt, using a lactonising agent such as methanesulfonic acid, phosphorous pentoxide, acidic ion-exchange resin, molecular sieves, acidic clay, silica gel and combinations thereof in a water miscible solvent like acetonitrile or immiscible solvent like dichloromethane at room temperature to bind water to form a insoluble complex which shifts the equilibrium towards lactone formation.

11. PCT Application No. WO 02/00615 A2 (P. Kumar; et. al) describes a method for lactonisation and isolation of Lovastatin (I) from the fermentation broth. The method comprises acidification of the broth with a mineral acid followed by lactonisation in an aqueous medium at 50-60° C. The broth is filtered and the mycelia cake extracted with an organic solvent, which is then concentrated to a reduced volume and subsequently filtered to give Lovastatin (I) having purity around 95%.

The method described in WO 02/00615 suffers from the following shortcomings in that, i) lactonisation of the hydroxy acid requires a long time between 20-60 hrs which is lengthy by any industrial manufacturing standard, ii) the method involves multiple unit operations, comprising initial lactonisation in an aqueous medium, followed by extraction with an organic solvent, Moreover, it was found that replication of the method described in WO 02/00615 gave Lovastatin (I) with only 54% yield, which needless to mention, is not an attractive commercial proposition.

12. U.S. Patent Application 2003/0050482 A1 (Lee K. H et al) relates to a method for isolation of Lovastatin (I) by lactonisation of the acid (II) or its ammonium salt in the presence of dehydrating agents like magnesium sulfate, sodium sulfate, calcium chloride, molecular sieves etc instead of an acidic medium in an inert atmosphere. Lactonisation of mevinolinic acid (II) is carried out at a very high temperature of 100-110° C. At this temperature, Lovastatin (I) is prone to degradation, giving rise to dimeric impurity, which is difficult to remove by conventional methods.

To summarise, the prior art methods for preparing Lovastatin (I) suffer from the following disadvantages:

i) They involve sequential steps of initial alkaline pretreatment, lactonisation of acid (II) after acidification, extraction of the lactonised product i.e., Lovastatin of formula (I) with a organic solvent followed by isolation of Lovastatin of formula (I), rendering the prior art methods lengthy and tedious, ii) Formation of higher level of impurities, which are difficult to remove by conventional purification methods, and iii) Utilization of expensive and highly sophisticated purification methods such as chromatography, reverse osmosis, ultrafiltration etc, and/or use of solvents like acetonitrile having low flash points.

Regulatory authorities all over the world are becoming very stringent about the level of impurities in an approved drug. Especially, there is a growing concern about the nature of impurities present in such molecules. Pharmacopoeial specification requires that the impurities such as the dimeric impurity in Lovastatin (I), which is difficult to remove by conventional methods, should be below 0.2%.

Needless, to mention most of the prior art methods do not give product conforming to the above mentioned criteria.

Therefore, there exists a need for a method for manufacture of lovastatin of the formula (I), which is not only simple, efficient, cost effective, but also gives Lovastatin (I) in high yield and purity, substantially free of impurities.

OBJECTS OF THE INVENTION

It is therefore, an object of the present invention to provide a method for the manufacture of Lovastatin of formula (I), which overcomes the shortcomings of the prior art methods.

Another object of the present invention is to provide a process for manufacture of Lovastatin (I) in high yield and purity utilising a simple, cost effective method which combines the steps of lactonisation and extraction with a hydrophobic solvent, thereby reducing the number of unit operations and time required for a single run.

Yet, another object of the invention is to reduce the time required for lactonisation of Mevinolinic acid (II) to Lovastatin (I) to approximately 15 hours, as opposed to between 20-60 hours, as reported in prior art.

A further object of the invention is to carry out the concurrent process of lactonisation and extraction of Lovastatin of formula (I) with a hydrophobic solvent, at a temperature between 40-60° C., wherein the formation of impurities associated with elevated temperatures are minimised and gives Lovastatin (I) in higher yield-and purity.

Yet, a further object of the invention is isolation of Lovastatin (I) of high purity by dissolving impure Lovastatin (I), in a chlorinated hydrocarbon and filtering the resinous impurities formed during lactonisation of compound (II) and fermentation of the broth. Isolating Lovastatin (I) by adding a non-polar hydrophobic solvent and distilling the chlorinated hydrocarbon followed by crystallization to give Lovastatin (I). Alternately, a mixture of a chlorinated hydrocarbon and a non-polar hydrophobic solvent is added to impure Lovastatin (I) and the resinous impurities filtered. Lovastatin (I) is isolated, by distilling the chlorinated solvent followed by crystallization to give Lovastatin (I). The compound (I) is further recrystallised from an aliphatic alcohol to obtain Lovastatin (I) substantially free from impurities and conforming to pharmacopoeial specification.

A further object of the invention relates to optional repurification of pure Lovastatin (I) by adding a water miscible solvent and alumina to pure lovastatin (I) and heating the mixture between 40-60° C., filtering the mixture and isolating extra pure Lovastatin (I), substantially free from impurities and conforming to pharmacopoeial specification.

SUMMARY OF THE INVENTION

One aspect of the present invention relates to a simple, efficient, cost effective method for manufacture of Lovastatin (I) in good yield and purity.

Another aspect of the invention relates to a method for manufacture of Lovastatin (I) comprising, i) adjusting the pH of the fermentation broth containing Mevinolinic acid (I) with a mineral acid to pH 3.5±0.10.

ii) heating the acidified fermentation broth or the mycelia cake in presence of a hydrophobic solvent and carrying out concurrent lactonisation, of Mevinolinic acid (II) to Lovastatin (I) and extraction of Lovastatin (I) into the hydrophobic solvent, at a temperature ranging between 40-60° C., preferably in an inert atmosphere, in a time period less than 20 hours.

iii) evaporating the organic layer after washing with an aqueous solution of an inorganic base followed by a water wash, and filtration to give impure Lovastatin (I), iv) isolating pure Lovastatin (I), by a) dissolving impure Lovastatin in a chlorinated solvent or a mixture of a chlorinated solvent and a non-polar hydrophobic solvent, and filtering resinous suspended impurities, b) adding a non-polar hydrophobic solvent to the filtrate containing Lovastatin (I), if the non-polar hydrophobic solvent is not previously added and heating the mixture between 40-60° C., optionally with carbon, and filtering, c) fractional distillation of the filtrate to remove the chlorinated solvent and crystallization from a non-polar hydrophobic solvent to give pure Lovastatin (I), d) Lovastatin is further recrystallised from an aliphatic alcohol to give lovastatin (I), substantially free from impurities and conforming to pharmacopoeial specification.

e) ptionally, further purifying pure Lovastatin (I) thus obtained by f) addition of pure Lovastatin (I) to a mixture of alumina and a water miscible solvent, g) heating the mixture between 50-60° C., and filtering, h) Crystallising extrapure Lovastatin (I) from the filtrate, to give extrapure Lovastatin (I), substantially free from impurities and conforming to pharmacopoeial specifications.

An important finding of the present invention is that lactonisation of step (i) at a pH higher or lower than 3.5±0.10 leads to formation of impurities, which eventually reduces the yield. The pH range of 3.5±0.10 was found to be ideal for obtaining optimum yield. This observation is contrary to literature reports, which recommend a pH range from 2.0 to 4.0.

Lactonisation of Mevinolinic acid (II) with simultaneous extraction of (I) into the hydrophobic solvent minimises degradation of Lovastatin (I) in acidic medium and also shift of equilibrium in favour of lactone formation is facile, thereby reducing impurity formation.

The presence of a hydrophobic solvent accelerates lactone formation contrary to prior art methods wherein the lactonisation is carried out in an aqueous medium, because of which the completion of the lactonisation reaction takes 20-60 hours.

The process of lactonisation is preferably carried out at 40-60° C., since higher temperature results in impurity formation, thereby decreasing the yield.

The time required for lactonisation is approximately 15 hours at 40-60° C. Prolonged time reduces the yield, presumably due to impurity formation. It is to be noted that the heating time and the benefits to be accrued thereby have not been reported in the prior art.

DETAILED DESCRIPTION OF THE INVENTION

The present invention will now be described in greeter detail with reference to the accompanying wherein FIG. 1 shows a schematic representation of lactonisation of Mevinolinic acid (II) and isolation of pure Lovastatin (I);

The method for manufacture of Lovastatin (I) as per the present invention is summarized in Scheme 1 below for ready reference, which comprises of:

A. Lactonisation of Mevinolinic acid (II) and isolation of impure Lovastatin (I), B. Purification of impure Lovastatin (I)

C. Optionally, repurifying pure Lovastatin (I) from a mixture of alumina and a water miscible solvent.

Scheme-I
LACTONISATION AND ISOLATION OF PURE LOVASTATIN (I)
A. Lactonisation of Mevinolinic acid (II) and isolation of impure Lovastatin (I).
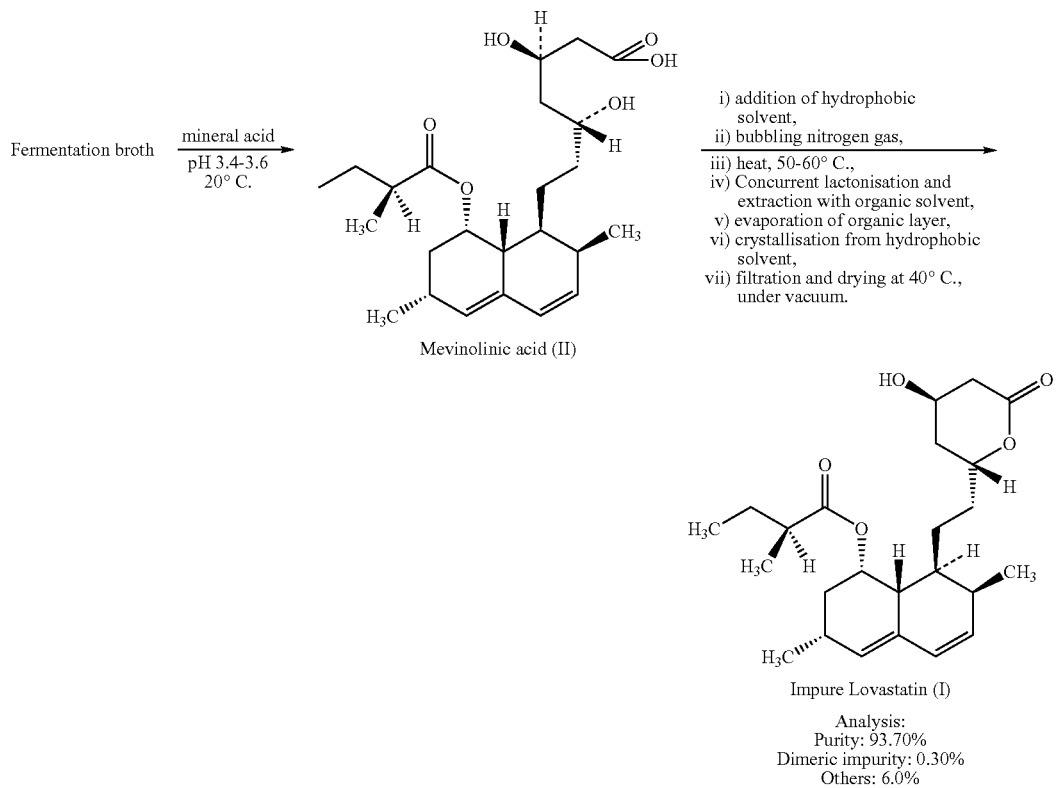
B. Purification of impure Lovastatin (I) [as obtained in A]
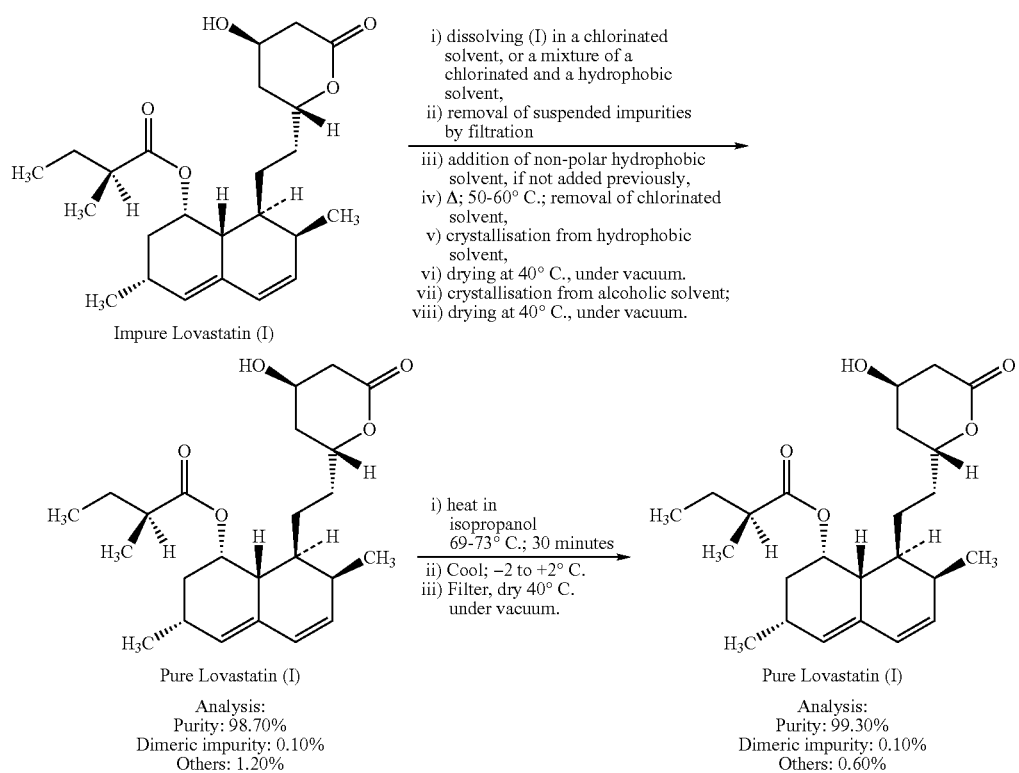

-continued
C. Optional repurification of Lovastatin (I) [optional repurification of lovastatin (I) as obtained in B]

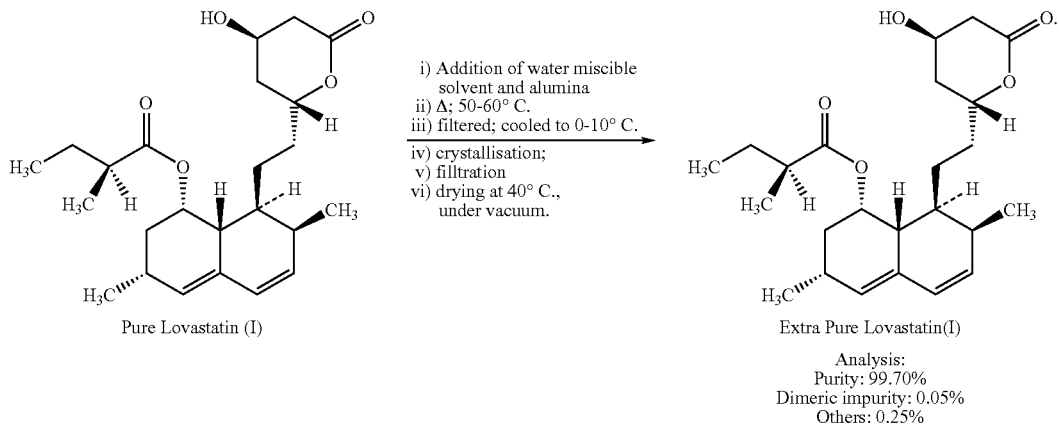

Pure Lovastatin (I)

i) Addition of water miscible solvent and alumina
ii) Δ; 50-60° C.
iii) filtered; cooled to 0-10° C.
iv) crystallisation;
v) filltration
vi) drying at 40° C., under vacuum.

Extra Pure Lovastatin(I)
Analysis:
Purity: 99.70%
Dimeric impurity: 0.05%
Others: 0.25%

Mevinolinic acid of formula (II), an intermediate of Lovastatin (I) is obtained through the process of fermentation of a culture broth, which is described in U.S. Pat. No. 4,231,938, U.S. Pat. No. 4,049,495 and U.S. Pat. No. 3,983,140.

The method practiced by the present inventors for preparing Mevinolinic acid (II) involves cultivating a microorganism known as *Aspergillus terreus* in an aqueous media containing sources of carbon, nitrogen and inorganic salts like dextrose, sucrose, sodium acetate, citric acid assimilable by the microorganism. The fermentation is carried out at 28-30° C., maintaining a pH of 5.9-6.3 for 220-260-hrs.

Figure 1:
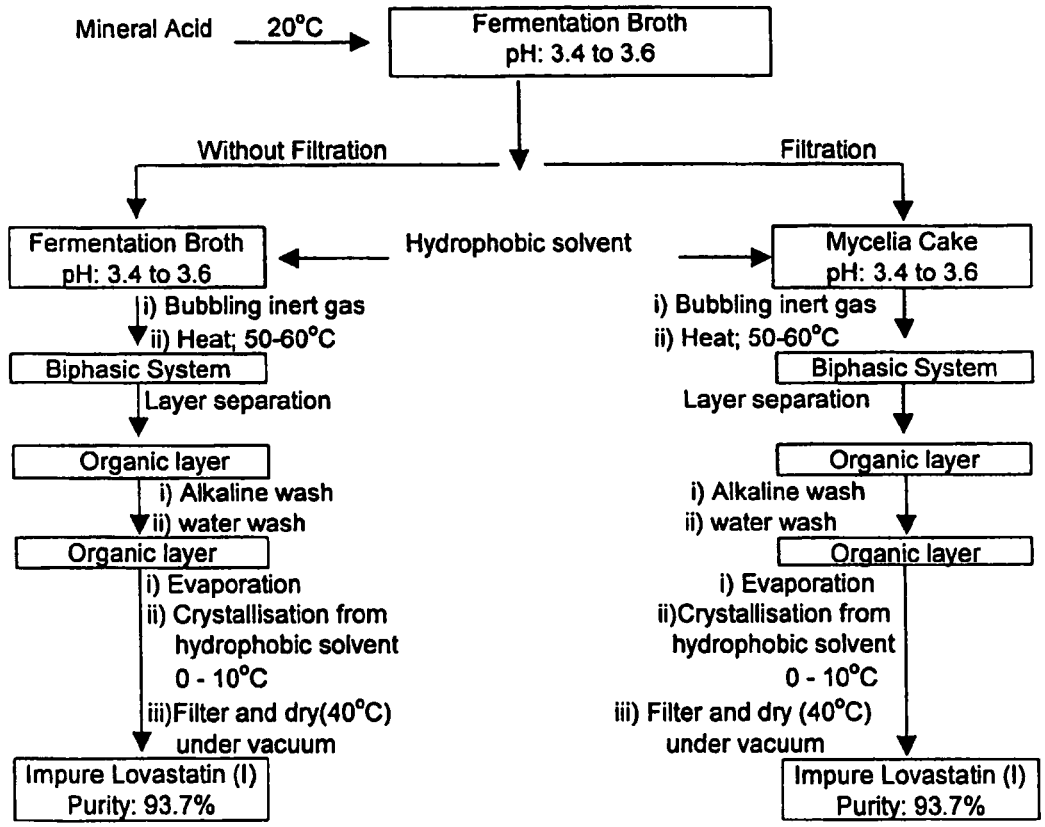
Figure 1:
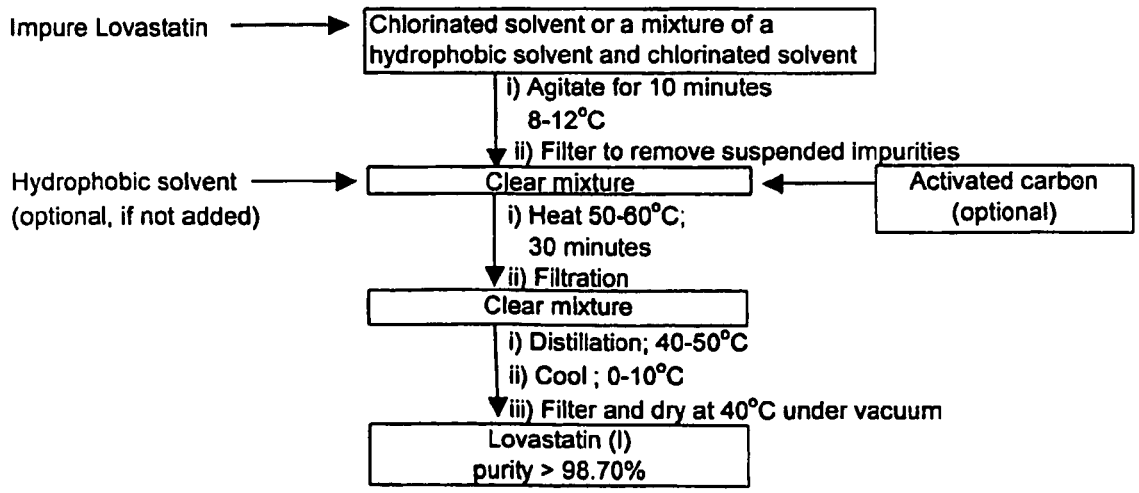

The fermentation of the culture broth gives Mevinolinic acid of formula (II). A flow diagram of the operations for lactonisation of Mevinolinic acid (II) to Lovastatin (I) and its isolation and purification is shown in FIG. 1, the details of which are given herein below:

A. Isolation of Impure Lovastatin (I)

The fermentation broth is cooled to a temperature between 15 to 25° C., but preferably 20° C. and the pH is adjusted between 3.0 to 4.0 but preferably 3.5±0.10 with a mineral acid. The mineral acid is selected from hydrochloric acid, sulphuric acid, orthophosphoric acid but preferably orthophosphoric acid. The pH at which the lactonisation is carried out is significant for the yield and quality of Lovastatin (I).

The yield of Lovastatin (I) is higher at pH 3.5 while it is lower at pH 2.0 due to impurity formation, which reduces the yield. The yield is the lowest at pH 4.5 as the rate of lactonisation is slow. The pH range of 3.4 to 3.6 was selected, as the yields were higher in this range.

Figure 2:
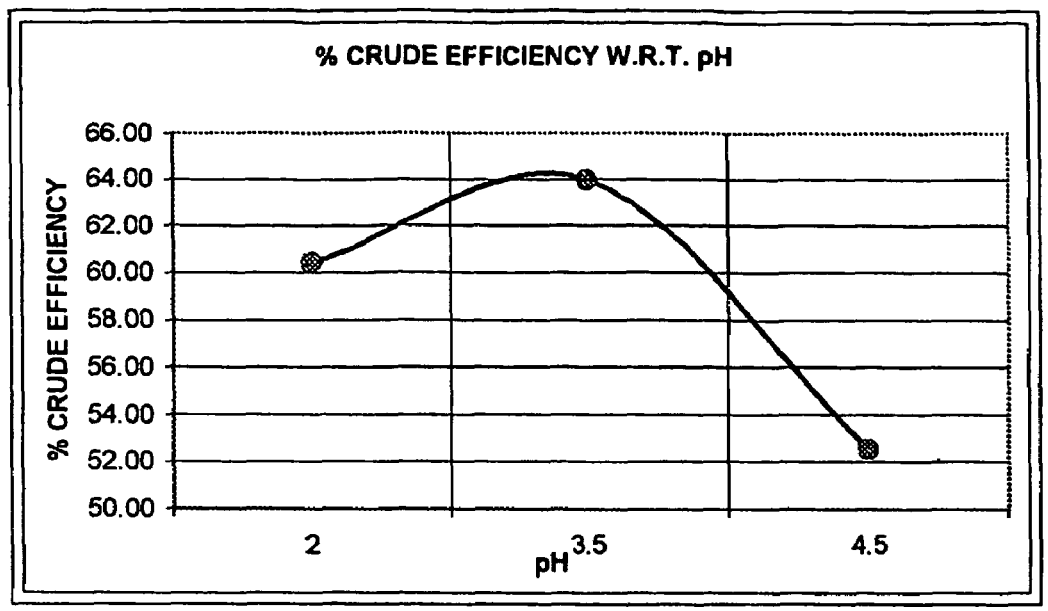
FIG. 2 shows the effect of pH on the isolated yield.

The effect of pH on the isolated yield is shown in FIG. 2.

A hydrophobic solvent selected from aromatic hydrocarbons like toluene, xylene; chlorinated solvents like dichloroethane, chloroform; but preferably aromatic hydrocarbon like toluene is added to the broth or the mycelia cake obtained after filtration to form a biphasic system. The mixture is heated in the range 55±5° C. for 12.0 hours, in an inert atmosphere free from oxygen when complete lactonisation takes place.

Figure 3:
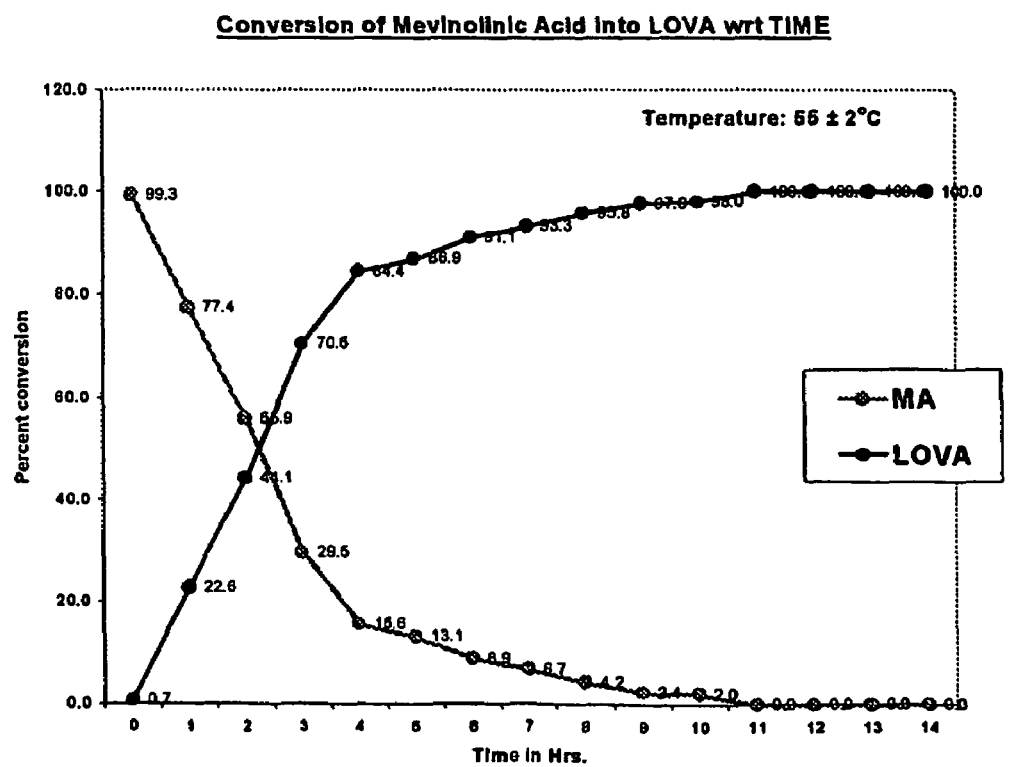
FIG. 3 shows a graphical representation of the time required to complete lactonisation.

The rate of conversion of Mevinolinic acid (II) into Lovastatin (I) was studied, and it was found that unlike prior art methods, which take 20-60 hours, the present method required only 11 hours for the aforesaid conversion to take place. The time required for complete lactonisation is shown graphically in FIG. 3.

The effect of temperature on the rate of lactonisation revealed that heating the biphasic system at higher temperatures above 85° C. leads to higher amount of impurity formation, while lactonisation is slower at lower temperatures, i.e. below 30° C. and, also layer separation is difficult.

The inert atmosphere can be nitrogen, helium, argon but preferably nitrogen. Nitrogen gas is bubbled into the reaction mixture and the mixture heated between 40-60° C.

Surprisingly, it has been observed that if the lactonisation is carried out in an inert atmosphere, the overall yield of isolation of (I) is increased by 4-5%. Thus, in an inert atmosphere, the yield of (I) at step (A) is 76.76%, while in the absence of nitrogen atmosphere it is 71.41%.

There is no such observation in literature about the significant effect of an inert atmosphere on the yield of Lovastatin (I).

The organic layer is separated and optionally the aqueous broth or the mycelia cake is again extracted with toluene and extracted at 55±5° C. in an inert atmosphere. Alternately, the organic layer is decanted from the mixture containing the mycelia cake, and the mycelia cake, is optionally again extracted with toluene in an inert atmosphere.

It has been also observed that time required for lactonisation has a profound effect on the yield. The process of lactonisation and extraction is carried out for not more than 20 hours as the product has got a tendency to degrade and form impurities on prolonged heating. This is reflected in the reduced yield of impure Lovastatin (I) (Table-I)

TABLE-I

| Heating time (hrs) | % Isolated Yield of (I) at stage (A) |
|---|---|
| 19 hours | 70.6% |
| 22 hours | 55.6% |

The organic layer obtained after extraction of the fermentation broth or the mycelia cake is agitated with an aqueous solution of an inorganic base which is selected from alkali carbonates, alkali bicarbonates, alkali hydroxides but preferably alkali bicarbonates. The alkali bicarbonates are selected from sodium bicarbonate, potassium bicarbonate but preferably sodium bicarbonate. The concentration of the alkali bicarbonates can be between 1.5-5.0% preferably 2.5% sodium bicarbonate solution.

The volume of sodium bicarbonate solution is between 5.0-15.0% of the total volume of the organic layer, but preferably 10%.

The organic layer is washed with sodium bicarbonate solution at least once followed by water washing to remove inorganic salts and impurities.

The organic layer is distilled under reduced pressure between 30 to 45° C. preferably 35-40° C., and the residue is crystallized from a hydrophobic solvent selected from toluene, xylene preferably toluene. The crystallized mass is filtered, washed with toluene and dried at 35-40° C. under vacuum.

Filtration of Lovastatin (I) slurry in toluene substantially removes non-polar impurities formed during fermentation and lactonisation of compound (II).

In a specific embodiment, the fermentation broth containing Mevinolinic acid of formula (II) was cooled to 20° C. and the pH of the mixture adjusted to 3.5±0.1 with 85% orthophosphoric acid and the broth optionally filtered.

Toluene was added to the broth or the mycelia cake. The volume of toluene added was 1.5 to 1.6 times volume by weight of the broth, preferably 1.4 times volume by weight of the fermentation broth.

Nitrogen gas was then bubbled into the mixture containing Mevinolinic acid of formula (II) and the mixture heated to 55±5° C. The mixture was agitated at the same temperature for 12.0 hours and the organic layer separated.

The fermentation broth or the mycelia cake is optionally further extracted with toluene to improve the efficiency of the batch process.

The organic extracts containing Lovastatin (I) thus obtained were combined and washed with 2.5% sodium bicarbonate solution, the volume of the bicarbonate solution used was 10% of the total organic layer.

The organic layer was separated and washed with water, the volume of Water taken being 10% of the volume of the combined organic extracts.

The organic layer was distilled under reduced pressure between 35-40° C., and Lovastatin (I) was isolated from the residue by adding a organic solvent preferably toluene. The volume of toluene added is selected from between 3-8% volume of the organic layer distilled, preferably 4-6% volume of the total volume of the organic layer distilled. The mixture was cooled between (0±10° C.) preferably (−5±1° C.), stirred for a period between 2-10 hours preferably 4.0 hours and filtered. The wet cake was washed with chilled toluene (0° C.) and the wet cake dried between 30-40° C.

B. Purification of Lovastatin (I)

Generally, Lovastatin (I) isolated after lactonisation by any method, needs further purification as it contains oily resinous mass, nutrients added during cultivation of the fermentation broth, and related impurities introduced during fermentation and subsequent lactonisation of the hydroxy acid (II). The product (I) thus obtained therefore needs further purification.

The present invention provides a method for purification, which purifies Lovastatin (I) by a simple method involving readily available solvents and which are non-hazardous for industrial use.

Impure Lovastatin (I) obtained by lactonisation of Mevinolinic acid (II) from the fermentation broth in an acidic medium is purified from a mixture of chlorinated solvent and a hydrophobic solvent.

Lovastatin (I) is dissolved in a chlorinated hydrocarbon solvent, which is selected from dichloromethane, dichloroethane but preferably dichloromethane. The volume of dichloromethane added is between 1-10 times, preferably 2-7 times, the weight of lovastatin (I) taken for purification. The mixture is stirred for 5-30 minutes preferably 10 minutes to dissolve the compound. Insoluble suspended resinous impurities are filtered and the filtrate is diluted with a hydrophobic solvent preferably an aromatic hydrocarbon selected from toluene, xylene preferably toluene. Toluene is added to the clear mixture and after optional carbon treatment the mixture is heated at 55±5° C. and filtered. The volume of toluene added is between 2-8 times the weight of the input preferably 4-6 times volume/weight of the input. The filtrate is concentrated and Lovastatin (I) is crystallised from an aromatic hydrocarbon preferably toluene. The volume of toluene added is between 4-6% of the total organic layer. Mixture is cooled between (0-10° C.) preferably (3±2° C.) and filtered. The wet cake is washed with toluene and dried at 30-40° C. under vacuum.

Alternately, Lovastatin (I) is dissolved in a mixture of toluene and dichloromethane in the same proportions and after optional carbon treatment the mixture containing (I) is filtered to remove resinous impurities. The filtrate is then distilled and Lovastatin (I) is crystallised from an aromatic hydrocarbon preferably toluene. Mixture is cooled between (0-10° C.) preferably (3±2° C.) and filtered. The wet cake is washed with toluene and dried at 30-40° C. under vacuum.

In a specific embodiment, impure Lovastatin (I) is added to dichloromethane. The mixture is stirred for 10 minutes for the compound to dissolve. Insoluble suspended resinous impurities are filtered and the clear mixture is diluted with toluene. The volume added is 5 times the weight of the batch-size. The mixture is optionally treated with carbon at 55±5° C. and filtered. The mixture is concentrated and Lovastatin (I) is crystallised from an aromatic hydrocarbon preferably toluene. Mixture is cooled between (3±2° C.) and filtered. The wet cake is washed with toluene and dried at 30-60° C.

The aforesaid method of purification is repeated at least twice to obtain Lovastatin (I) with purity above 99.0%, substantially free of impurities and conforming to pharmacopoeial specification.

The compound (I) thus obtained is further purified by crystallization from an aliphatic alcohol. The alcohol is selected from methanol, ethanol and isopropanol preferably isopropanol. The volume of isopropanol is between 4-10 times the amount of (I) but preferably 6 parts of isopropyl alcohol. The mixture is heated at 60-80° C. but preferably, 71±2° C. for a period of 15 to 45 minutes but preferably 30 minutes. The mixture is cooled to between −5 and +5° C., but preferably 0±2° C. and stirred for 1 to 3 hours, but preferably 2 hours for complete crystallization of pure Lovastatin of formula (I). The crystalline mixture is filtered and washed with isopropanol. The wet cake is dried at 35-40° C. under vacuum.

In a specific embodiment, lovastatin (I) obtained after the first purification is heated with isopropanol (6 times the batch size) at 71±2° C. for 30 minutes and cooled to 0±2° C. The mixture was stirred at the same temperature for 2 hours for complete crystallization of lovastatin (I). The mixture was filtered and washed with isopropanol. The wet cake was dried at 35-40° C. under vacuum.

This method of purification is optionally repeated to obtain Lovastatin (I) with purity above 99.30%, substantially free of impurities and conforming to pharmacopoeial specification.

Thus, the present inventors have found a simple cost-effective method for purification, which, employs non-hazardous solvents and can be used for industrial manufacture.

C. Repurification of Pure Lovastatin (I).

Optionally the product (I) obtained in step B) is further purified by agitating the compound in a mixture of water miscible organic solvent and alumina at a temperature between 50-60° C. Alumina used is basic, acidic, or neutral. The water miscible organic solvent is selected from alcohol, ketones, nitrites preferably ketone and alcohol or a mixture thereof. The ketone is selected from acetone, methyl ethyl ketone, methyl isobutyl ketone but preferably acetone. The alcohol is selected from methanol, ethanol, isopropanol, n-butanol preferably isopropanol.

Lovastatin is stirred in acetone at 50-60° C. The volume of acetone added is between 5-10 times preferably 7.0 times. Alumina is added to the clear mixture and agitated at the same temperature for 45-75 minutes preferably 60 minutes. The mixture is filtered, and the filtrate is cooled to 0±2° C. and pure Lovastatin (I) is allowed to crystallise. The product is filtered, washed with chilled acetone and dried at 40-60° C.

The purity of Lovastatin (I), obtained after repurification of the pure Lovastatin (I), has purity above 99.5 %. The impact of the purification method in removing impurities is evident from the data shown in (Table-II).

TABLE-II

| No | Lovastatin (I) | Lovastatin (I) Impurities | | | | | |
|---|---|---|---|---|---|---|---|
| | | Unknown-1 | Unknown-2 | Unknown-3 | Dimer | Dihydro | Assay |
| 1 | Impure (I) | 0.15 | 0.16 | 0.27 | 0.25 | 5.40 | 93.70 |
| 2 | Purified by Dichloromethane/ Toluene method | 0.10 | 0.14 | <0.05 | 0.10 | 0.46 | 99.50 |
| 3 | Alumina/water miscible solvent | 0.10 | 0.09 | <0.05 | 0.06 | 0.20 | 99.70 |

All the impurities, which were present in impure Lovastatin (I), after the process of fermentation and lactonisation have been substantially removed below specified pharmacopoeial limits by a purification method using dichloromethane and toluene. Optional, further purification of the product has resulted in a highly pure product (I) free from impurities carried forward from the fermentation stage and also those formed during lactonisation of Mevinolinic acid (II) to Lovastatin (I).

The invention can be further illustrated by the following examples, which, however, should not be construed as limiting the scope of the invention.

EXAMPLE 1

Lactonisation of Mevinolinic Acid (II) to Impure Lovastatin (I)

(Broth Extraction Process)

Lovastatin broth [4500 gms; containing (34.2) gms of mevinolinic acid (II)] was added into a flask and cooled to 20° C., and the pH was adjusted to 3.5±0.1 by addition of 85% orthophosphoric acid (60 gms). Toluene (11250 ml) was added and the mixture agitated to 55±5° C. for 19.0 hours in a nitrogen atmosphere. The organic layer was separated and washed twice with 2.5% aqueous sodium bicarbonate solution (580 ml). The organic layer was washed with water (580 ml) and the organic layer concentrated under vacuum at 35-40° C. Toluene (260 ml) was added to the residue and the mixture was cooled to −5° C. for complete crystallization of Lovastatin (I) in a period of 4.0 hours. The mixture was filtered and the wet cake washed with chilled toluene (50 ml). The wet cake was dried at 35-40° C. to give impure Lovastatin (I) 26.6 gm; % Yield 76.12; % purity 93.7.

EXAMPLE-2

Lactonisation of Mevinolinic acid (II) to Impure Lovastatin (I)

(Cake Extraction Process)

Lovastatin broth [4500 gms; containing (34.2) gms of mevinolinic acid (II)] was added in a flask. The broth was cooled to 20° C. and the pH of the mixture adjusted to 3.5±0.01 by adding 85% orthophosphoric acid (60 gms). The broth was filtered and toluene (6200 ml) was added to the mycelia cake. The mixture was agitated at 55±5° C. for 19 hours in a nitrogen atmosphere. The organic layer was separated and washed twice with 2.5% aqueous sodium bicarbonate solution (580 ml). The organic layer was separated and washed with water (580 ml) and concentrated. Toluene (260 ml) was added to the residue and cooled to −5° C. The mixture was agitated at same temperature for 4.0 hours for complete crystallization of Lovastatin (I). The mixture was filtered and washed with chilled toluene (50 ml). The wet cake was dried at 35-40° C. to give impure Lovastatin (I) 26.6 gm; % Yield: 76.12; purity 93.7%.

EXAMPLE-3

Purification of Lovastatin (I)

Dichloromethane (245 ml) was added to a clean dry flask. Impure Lovastatin (I) (122.5 gms) purity 93.7% as obtained in example (1) or example (2) was added followed by addition of toluene (245 ml) and 2.45 gm activated charcoal. The mixture was heated at 55±5° C. for 30 minutes and filtered. The carbon cake was washed with dichloromethane (50 ml). The mixture was distilled below 35° C. to completely remove dichloromethane. The residue was cooled to 5±1° C. and stirred for 2.0 hours. The crystalline mixture was filtered and the product was washed with chilled toluene (50 ml). The product was dried at 35-40° C. under vacuum. Yield: 110.3 gms; % Yield: 93.88; Purity: 97.70%.

EXAMPLE-4

Purification of Lovastatin (I)

Dichloromethane (490 ml) was added to a clean dry flask and cooled to 10±2° C. Impure Lovastatin (I) (122.5 gms) purity 93.7% as obtained in example (1) or example (2) was added and stirred at 10±2° C. Insoluble suspended impurities were filtered. Toluene (200 ml) was added to the mixture followed by addition of activated carbon (2.45 gms). The mixture was heated at 55±5° C. for 30 minutes and filtered.

The carbon cake was washed with dichloromethane (50 ml). The mixture was distilled below 35° C. to completely remove dichloromethane. The residue was cooled to 5±1° C. and stirred for 2.0 hours. The crystalline mixture was filtered and the product (I) was washed with chilled toluene (50 ml). The product (I) was dried at 35-40° C. under vacuum. Yield: 109.1 gms; % Yield: 93.9; Purity: 98.80%.

EXAMPLE-5

Purification of Lovastatin (I)

Dichloromethane (441 ml) was added to a clean dry flask and cooled to 10±2° C. Lovastatin (I) (110.3 gms) purity 97.7% as obtained in example (3) was added and stirred at 10±2° C. Insoluble suspended impurities were filtered. Toluene (222 ml) was added to the mixture. The mixture was distilled below 35° C. to completely remove dichloromethane. The residue was cooled to 5±1° C. and stirred for 2.0 hours. The crystalline mixture was filtered and the product was washed with chilled toluene (50 ml). The product was dried at 35-40° C. under vacuum. Yield: 106.7 gms; % Yield: 97.73; Purity: 98.70%.

EXAMPLE-6

Purification of Lovastatin (I)

Dichloromethane (213 ml) was added to a clean dry flask. Impure Lovastatin (I) (106.7 gms) purity 98.7% as obtained in example (5) was added followed by addition of toluene (213 ml). The mixture was heated at 55±5° C. for 30 minutes and filtered. The carbon cake was washed with dichloromethane (50 ml). The mixture was distilled below 35° C. to completely remove dichloromethane. The residue was cooled to 5±1° C. and stirred for 2.0 hours. The crystalline mixture was filtered and the product was washed with chilled toluene (50 ml). The product was dried at 35-40° C. under vacuum. Yield: 104.69 gms; % Yield: 98.51; Purity: 99.1%.

EXAMPLE-7

Purification of Lovastatin (I)

Acetone (628 ml) was added to a clean dry flask. Lovastatin (104.69 gms) of purity 99.1% as obtained in example (6) was added to the flask and heated to 55±5° C. Basic alumina (10.5 gms) was added to the mixture and stirred at 55±5° C. for 60 minutes. The mixture was filtered through hyflo pad and washed with acetone (42.5 ml). The filtrate was cooled to 0±2° C. and stirred for 2.0 hours. The crystalline mixture was filtered and washed with acetone (42.5 ml). The wet cake was dried at 35-40° C. under vacuum. Yield: 91.6 gms; % Yield: 88.0; Purity: 99.70%.

EXAMPLE-8

Purification of Lovastatin (I)

Acetone (628 ml) was added to a clean dry flask. Lovastatin (104.69 gms) of purity 99.1% as obtained in example (6) was added to the flask and heated to 55±5° C. Acidic alumina (10.5 gms) was added to the mixture and stirred at 55±5° C. for 60 minutes. The mixture was filtered through hyflo pad and washed with acetone (42.5 ml). The filtrate was cooled to 0±2° C. and stirred for 2.0 hours. The crystalline mixture was filtered and washed with acetone (42.5 ml). The wet cake was dried at 35-40° C. under vacuum. Yield: 91.7 gms; % Yield: 88.1; % Purity: 99.70.

EXAMPLE-9

Purification of Lovastatin (I)

Acetone (628 ml) was added to a clean dry flask. Lovastatin (104.69 gms) of purity 99.1% as obtained in example (6) was added to the flask and heated to 55±5° C. Neutral alumina (10.5 gms) was added to the mixture and stirred at 55±5° C. for 60 minutes. The mixture was filtered through hyflo pad and washed with acetone (42.5 ml). The filtrate was cooled to 0±2° C. and stirred for 2.0 hours. The crystalline mixture was filtered and washed with acetone (42.5 ml). The wet cake was dried at 35-40° C. under vacuum. Yield: 91.9 gms; % Yield: 88.3; % Purity: 99.70.

EXAMPLE-10

Purification of Lovastatin (I)

Isopropanol (640 ml) was added to a clean dry flask. Lovastatin (106.7 gms) of purity 98.7% as obtained in example (5) was added to the flask and heated to 71±2° C. The mixture was stirred at 71±2° C. for 30 minutes. The mixture was slowly cooled to 0±2° C. and stirred for 2.0 hours. The crystalline mixture was filtered and washed with isopropanol (43.5 ml). The wet cake was dried at 35-40° C. under vacuum. Yield: 102.2 gms; % Yield: 96.4; % Purity: 99.30.

The invention claimed is:

1. A method for lactonisation of mevinolinic acid of formula II and isolation of Lovastatin of formula (I):

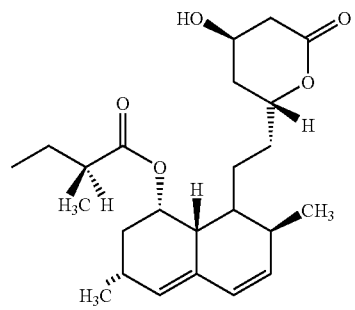

which comprises the steps of:
a) adjusting the pH of a fermentation broth containing mevinolinic acid(II) to 3.5±0.1 with a mineral acid, and optionally filtering the fermentation broth,
b) adding a hydrophobic solvent to the aqueous fermentation broth or the mycelia cake and bubbling an inert gas into the biphasic mixture,
c) heating the fermentation broth or the mycelia cake at 55±5° C., in the presence of a hydrophobic solvent, carrying out lactonisation of mevinolinic acid (II)

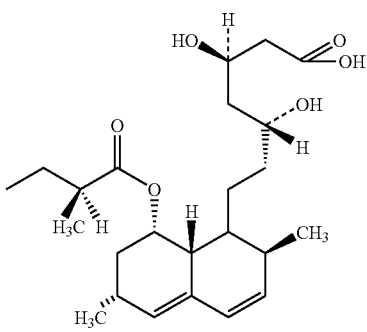

and extracting Lovastatin(I) into a hydrophobic solvent, concurrently, in a time period between 12-19 hours, under constant nitrogen bubbling, d) isolating impure Lovastatin (I) from said hydrophobic solvent, e) purifying impure Lovastatin (I) by dissolving impure Lovastatin (I) in a chlorinated solvent followed by removal of suspended resinous impurities by filtration, adding a hydrophobic solvent, heating the mixture to 55±5° C., evaporating the chlorinated solvent followed by crystallization from a hydrophobic solvent to give pure Lovastatin (I) of purity≧98.70%, or by dissolving Lovastatin (I) in a mixture of a chlorinated solvent and a hydrophobic solvent, filtering the suspended impurities, and heating the mixture to 55±5° C., followed by evaporating the chlorinated solvent and crystallizing from the hydrophobic solvent to give pure Lovastatin (I) of purity≧98.70%, f) recrystallising Lovastatin (I), from a aliphatic alcohol, by heating Lovastatin (I) with an aliphatic alcohol between 65 to 75° C. for 30 minutes, cooling the mixture between −5 to +5° C. and filtering crystalline Lovastatin (I) followed by drying at 35-40° C. to give pure Lovastatin (I) of purity≧99.3%, substantially free from impurities and conforming to pharmacopoeial specification.

2. A method as claimed in claim 1, wherein said pure Lovastatin (I) is further purified by heating said pure Lovastatin in the presence of alumina in a water miscible solvent at a temperature in the range of 50-60° C., filtering the mixture and crystallizing extrapure Lovastatin (I) of purity ≧99.5% conforming to pharmacopoeial specification.

3. A method as claimed in claim 1, wherein said steps of lactonisation and concurrent extraction by a hydrophobic solvent are carried out in a time period of not more than 20 hours.

4. A method as claimed in claim 1, wherein the acid used for adjusting the pH is a mineral acid.

5. A method as claimed in claim 4, wherein said mineral acid is hydrochloric acid, sulphuric acid, nitric acid or orthophosphoric acid.

6. A method as claimed in claim 1, wherein said hydrophobic solvent is selected from aliphatic hydrocarbon, aromatic hydrocarbon, and chlorinated hydrocarbon.

7. A method as claimed in claim 1, wherein said lactonisation of melvinolinic acid (II) and extraction of Lovastatin (I) is carried out at a temperature in the range of 50-60° C.

8. A method as claimed in claim 1, wherein the inert gas bubbled in the reaction medium is selected from nitrogen, argon and helium.

9. A method as claimed in claim 1, wherein said chlorinated solvent required for dissolving impure Lovastatin (I) is selected from dichloromethane, 1,2-dichloroethane and chloroform.

10. A method as claimed in claim 1, wherein said aliphatic alcohol employed for recrystallisation of Lovastatin (1) is isopropanol.

11. A method as claimed in claim 2, wherein the water miscible solvent is selected from ketonic solvent and an alcoholic solvent.

12. A method as claimed in claim 11, wherein said ketonic solvent is acetone.

13. A method as claimed in claim 12, wherein said alcoholic solvent is isopropanol.

14. A method as claimed in claim 2, wherein said alumina is selected from acidic alumina, basic alumina, neutral alumina.

* * * * *